US012594371B2

(12) United States Patent
Casey et al.

(10) Patent No.: US 12,594,371 B2
(45) Date of Patent: Apr. 7, 2026

(54) ASPIRATION VACUUM SOURCE

(71) Applicant: Neuravi Limited, Galway (IE)

(72) Inventors: Brendan Casey, Galway (IE); David Vale, Barna (IE)

(73) Assignee: NEURAVI LIMITED, Galway (IE)

( * ) Notice: Subject to any disclaimer, the term of this patent is extended or adjusted under 35 U.S.C. 154(b) by 108 days.

(21) Appl. No.: 18/441,734

(22) Filed: Feb. 14, 2024

(65) Prior Publication Data

US 2024/0277358 A1 Aug. 22, 2024

Related U.S. Application Data

(60) Provisional application No. 63/447,506, filed on Feb. 22, 2023.

(51) Int. Cl.
*A61M 1/00* (2006.01)
*A61B 17/00* (2006.01)
(Continued)

(52) U.S. Cl.
CPC ............... *A61M 1/75* (2021.05); *A61B 17/22* (2013.01); *A61B 17/221* (2013.01); *A61M 1/842* (2021.05);
(Continued)

(58) Field of Classification Search
CPC .......... A61M 1/71; A61M 1/75; A61M 1/842; A61M 25/003; A61M 25/0068; A61M 25/0074; A61M 25/0158; A61M 2025/0002; A61M 2025/0004; A61M 2025/0031; A61M 2025/0039; A61M 2025/0059; A61M 2025/1052; A61M 2205/3327; A61M 2205/3351; A61B 17/22; A61B 17/221; A61B 2017/00022; A61B 2017/00154; A61B 2017/00172;
(Continued)

(56) References Cited

U.S. PATENT DOCUMENTS

2002/0198550 A1 12/2002 Nash et al.
2004/0019310 A1 1/2004 Hogendijik
(Continued)

FOREIGN PATENT DOCUMENTS

WO 2014151209 A1 9/2014

*Primary Examiner* — Robert A Lynch
(74) *Attorney, Agent, or Firm* — Troutman Pepper Locke LLP

(57) ABSTRACT

An aspiration vacuum source comprises a vessel having a positive pressure fluid chamber and a vacuum chamber. The vacuum source having a primary tubing, and the positive pressure fluid chamber connected in fluid communication with the primary tubing via an auxiliary tubing. A fluid piston is slidably received within the positive pressure fluid chamber. A vacuum piston is slidably received within the vacuum chamber and produces a vacuum within the vacuum chamber upon movement of the vacuum piston. The fluid piston and the vacuum piston are each fixedly attached to be movable together within the positive pressure fluid chamber and the vacuum chamber, respectively. A secondary tubing is connected in fluid communication to the vacuum chamber. A manual pump is connected in fluid communication with the primary tubing. A vacuum is producible in the vacuum chamber in response to repeated manipulation of the manual pump.

18 Claims, 4 Drawing Sheets

(51) Int. Cl.

| | |
|---|---|
| *A61B 17/22* | (2006.01) |
| *A61B 17/221* | (2006.01) |
| *A61M 25/00* | (2006.01) |
| *A61M 25/01* | (2006.01) |
| *A61M 25/10* | (2013.01) |

(52) U.S. Cl.
CPC ............... *A61B 2017/00022* (2013.01); *A61B 2017/00154* (2013.01); *A61B 2017/00172* (2013.01); *A61B 2017/0023* (2013.01); *A61B 2017/00292* (2013.01); *A61B 2017/00367* (2013.01); *A61B 2017/00398* (2013.01); *A61B 2017/00544* (2013.01); *A61B 2017/00561* (2013.01); *A61B 2017/00862* (2013.01); *A61B 2017/00867* (2013.01); *A61B 2017/22067* (2013.01); *A61B 2017/22079* (2013.01); *A61B 2017/2212* (2013.01); *A61B 2017/2215* (2013.01); *A61B 2217/005* (2013.01); *A61M 2025/0002* (2013.01); *A61M 2025/0004* (2013.01); *A61M 25/003* (2013.01); *A61M 2025/0031* (2013.01); *A61M 2025/0039* (2013.01); *A61M 2025/0059* (2013.01); *A61M 25/0068* (2013.01); *A61M 25/0074* (2013.01); *A61M 25/0158* (2013.01); *A61M 2025/1052* (2013.01); *A61M 2205/3327* (2013.01); *A61M 2205/3351* (2013.01)

(58) Field of Classification Search
CPC .. A61B 2017/0023; A61B 2017/00292; A61B 2017/00367; A61B 2017/00398; A61B 2017/00544; A61B 2017/00561; A61B 2017/00862; A61B 2017/00867; A61B 2017/22067; A61B 2017/22079; A61B 2017/2212; A61B 2017/2215; A61B 2217/005

See application file for complete search history.

(56) References Cited

U.S. PATENT DOCUMENTS

| | | | |
|---|---|---|---|
| 2011/0034986 A1 | 2/2011 | Chou et al. | |
| 2016/0135829 A1 | 5/2016 | Holochwost et al. | |
| 2019/0239910 A1 | 8/2019 | Brady et al. | |
| 2020/0129751 A1* | 4/2020 | Malkowski | A61M 3/0237 |

\* cited by examiner

VACUUM/
ASPIRATION

TO CATHETER

FIG. 4A

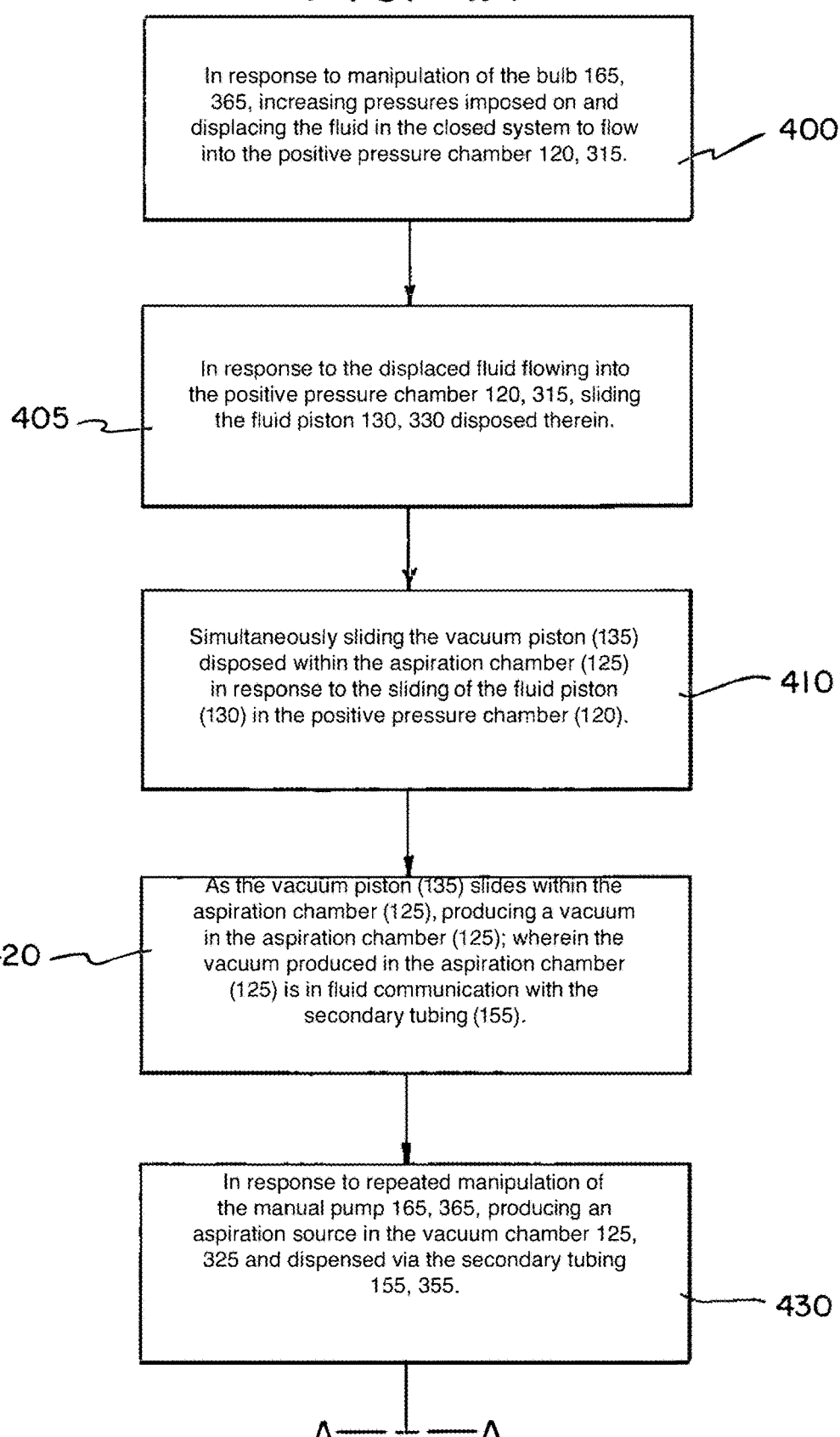

In response to manipulation of the bulb 165, 365, increasing pressures imposed on and displacing the fluid in the closed system to flow into the positive pressure chamber 120, 315.

— 400

In response to the displaced fluid flowing into the positive pressure chamber 120, 315, sliding the fluid piston 130, 330 disposed therein.

405 —

Simultaneously sliding the vacuum piston (135) disposed within the aspiration chamber (125) in response to the sliding of the fluid piston (130) in the positive pressure chamber (120).

— 410

As the vacuum piston (135) slides within the aspiration chamber (125), producing a vacuum in the aspiration chamber (125); wherein the vacuum produced in the aspiration chamber (125) is in fluid communication with the secondary tubing (155).

420 —

In response to repeated manipulation of the manual pump 165, 365, producing an aspiration source in the vacuum chamber 125, 325 and dispensed via the secondary tubing 155, 355.

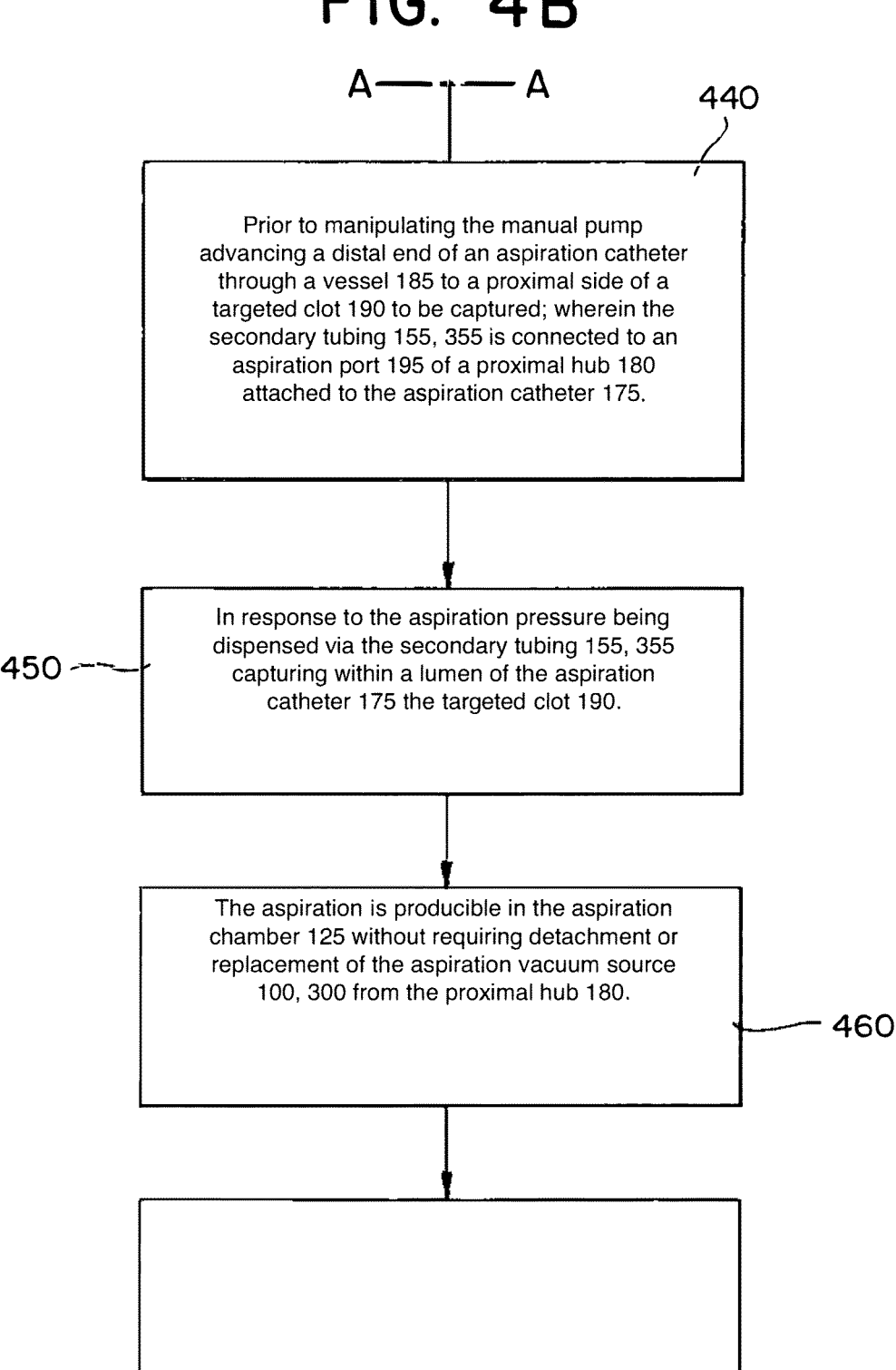

Prior to manipulating the manual pump advancing a distal end of an aspiration catheter through a vessel 185 to a proximal side of a targeted clot 190 to be captured; wherein the secondary tubing 155, 355 is connected to an aspiration port 195 of a proximal hub 180 attached to the aspiration catheter 175.

450

In response to the aspiration pressure being dispensed via the secondary tubing 155, 355 capturing within a lumen of the aspiration catheter 175 the targeted clot 190.

The aspiration is producible in the aspiration chamber 125 without requiring detachment or replacement of the aspiration vacuum source 100, 300 from the proximal hub 180.

460

ASPIRATION VACUUM SOURCE

CROSS-REFERENCE TO RELATED APPLICATION

This application claims the benefit of U.S. Provisional Patent Application No. 63/447,506 filed Feb. 22, 2023, the disclosure of which is incorporated herein by reference in its entirety.

FIELD

The present disclosure generally relates to systems and methods used during thrombectomy procedures for the capture and removal of occlusions or clots. Specifically, the present disclosure relates to an aspiration system for the capture and removal of occlusions or clots in a vessel where the aspiration pressure includes using a vacuum pressure source created from a positive pressure input.

BACKGROUND

Clots are essentially living polymers, comprising a matrix of intertwined and cross-linked fibrin strands within which are situated red and white blood cells, platelets and numerous other proteins and components. The mechanical properties of a clot are strongly influenced by the relative percentages of fibrin and red blood cells, and that clots with a high (and highly organized) fibrin content and low red blood cell content tend to be much firmer and more cohesive than clots of a higher red cell content. Such clots have also been found to have a higher coefficient of friction, or in other words to be "stickier". These firm and sticky clots can be very challenging to remove from a vessel.

Clots with a low fibrin content and high red cell content have been found to be less cohesive and more friable and to have a lower coefficient of friction than the more organized fibrin rich clots previously described. These properties mean that such clots may be easier to dislodge from the site of occlusion, but may tend to fragment during the retrieval process, with the consequent risk of loss of clot fragments into distal or new vascular territories.

Attempts to aspirate such clots into a catheter can be very challenging as the clot must be deformed to fit into the catheter lumen, and the energy required to deform such clots is not easily attained by aspiration. The high frictional coefficient of these clot types adds further to the challenge of aspirating them into the distal mouth of a catheter. Even maintaining a suction grip on such clots so that they can be retracted to the safety of a more proximal guide or sheath is very difficult, as these firm clots do not tend to deform and reshape easily and thus do not readily conform to the shape of the catheter tip to create a seal and consequent suction grip.

In an operation room ("OR"), a stand-alone aspiration pump may be used as source of aspiration. However, real estate in an OR setting can be difficult to achieve. In some settings, a syringe, such as, for example, a VacLok® vacuum pressure syringes may be used as a vacuum source. But the volume in a syringe is not large enough to create a sufficient vacuum. A user will need to use multiple vacuum syringes to create a sufficient vacuum source. In addition, some OR's may not have an aspiration source readily available. Thus, there is a need for an aspiration source that can be used in any OR setting, does not take up valuable real estate in an OR setting and that only relies on manual pressure to create a vacuum source sufficient for the needs of a thrombectomy removal surgery.

It is therefore desirable to develop a portable aspiration source that has as few active components as possible, that reduces the amount of real estate needed for use and that can create a vacuum source from a pressure source.

SUMMARY

In an example of the present disclosure, an aspiration vacuum source comprises a vessel having a positive pressure fluid chamber and a vacuum chamber. The vacuum source has a primary tubing, and the positive pressure fluid chamber connected in fluid communication with the primary tubing via an auxiliary tubing. The auxiliary tubing having a first valve disposed therein restricting flow therethrough to only flow upstream into the positive pressure fluid chamber. A fluid piston is slidably received within the positive pressure fluid chamber. The vacuum chamber is not in fluid communication with the positive pressure fluid chamber. A vacuum piston is slidably received within the vacuum chamber and produces a vacuum within the vacuum chamber upon movement of the vacuum piston. The fluid piston and the vacuum piston are each fixedly attached to a common shaft to be movable together within the positive pressure fluid chamber and the vacuum chamber, respectively. A secondary tubing is connected in fluid communication to the vacuum chamber through which the produced aspiration is dispensable therefrom. A manual pump is connected in fluid communication with the primary tubing; wherein a vacuum is producible in the vacuum chamber in response to repeated manipulation of the manual pump.

BRIEF DESCRIPTION OF THE DRAWINGS

The above and further aspects of this disclosure are further discussed with reference to the following description in conjunction with the accompanying drawings, in which like numerals indicate like structural elements and features in various figures. The drawings are not necessarily to scale, emphasis instead being placed upon illustrating principles of the disclosure. The figures depict one or more implementations of the disclosure devices, by way of example only, not by way of limitation.

FIGS. 4A and 4B are a flow chart illustrating a method of using a vacuum source in accordance with the present disclosure.

DETAILED DESCRIPTION

As used herein, the terms "about" or "approximately" for any numerical values or ranges indicate a suitable dimensional tolerance that allows the part or collection of components to function for its intended purpose as described herein. More specifically, "about" or "approximately" may refer to the range of values±20% of the recited value, e.g., "about 80%" may refer to the range of values from 61% to 99%.

As used herein, the term "microcatheter" is a catheter having a diameter that is small in comparison to catheters in cardiovascular applications, i.e., 8 French or less.

As used herein, the terms "cylindrical", "tubular" and "tube" are to be construed broadly and are not limited to a structure that is a right cylinder or strictly circumferential in cross-section or of a uniform cross-section throughout its length. For example, a tubular structure or system is generally illustrated as a substantially right cylindrical structure. However, the tubular system may have a tapered or curved outer surface without departing from the scope of the present disclosure.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

Figures 1A, 1B:
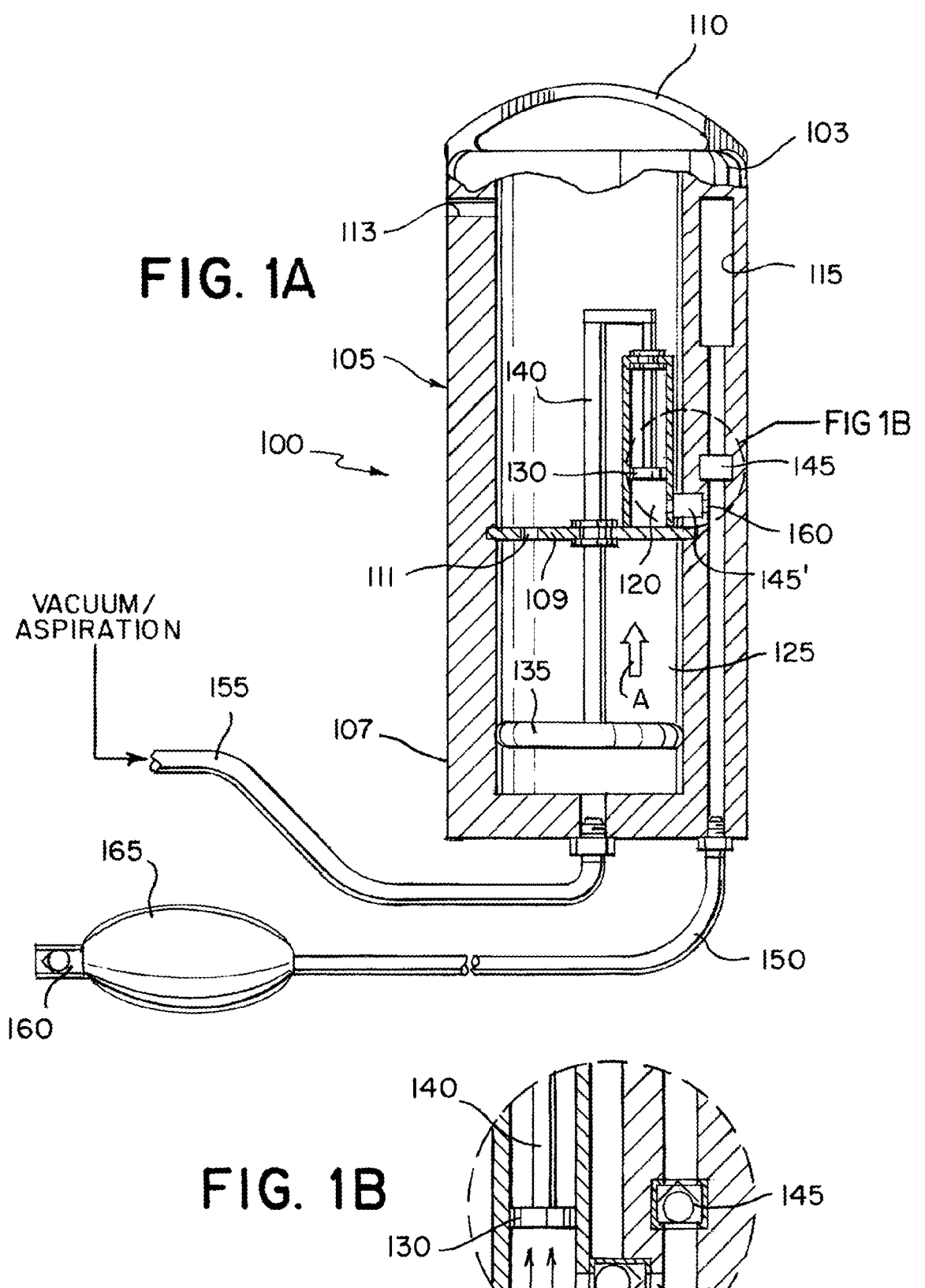
FIG. 1A is a partial cross-sectional view showing the aspiration vacuum source according to aspects of the present disclosure.
FIG. 1B is an enlarged view of circle labeled as FIG. 1B in FIG. 1A.
Figures 2, 3:
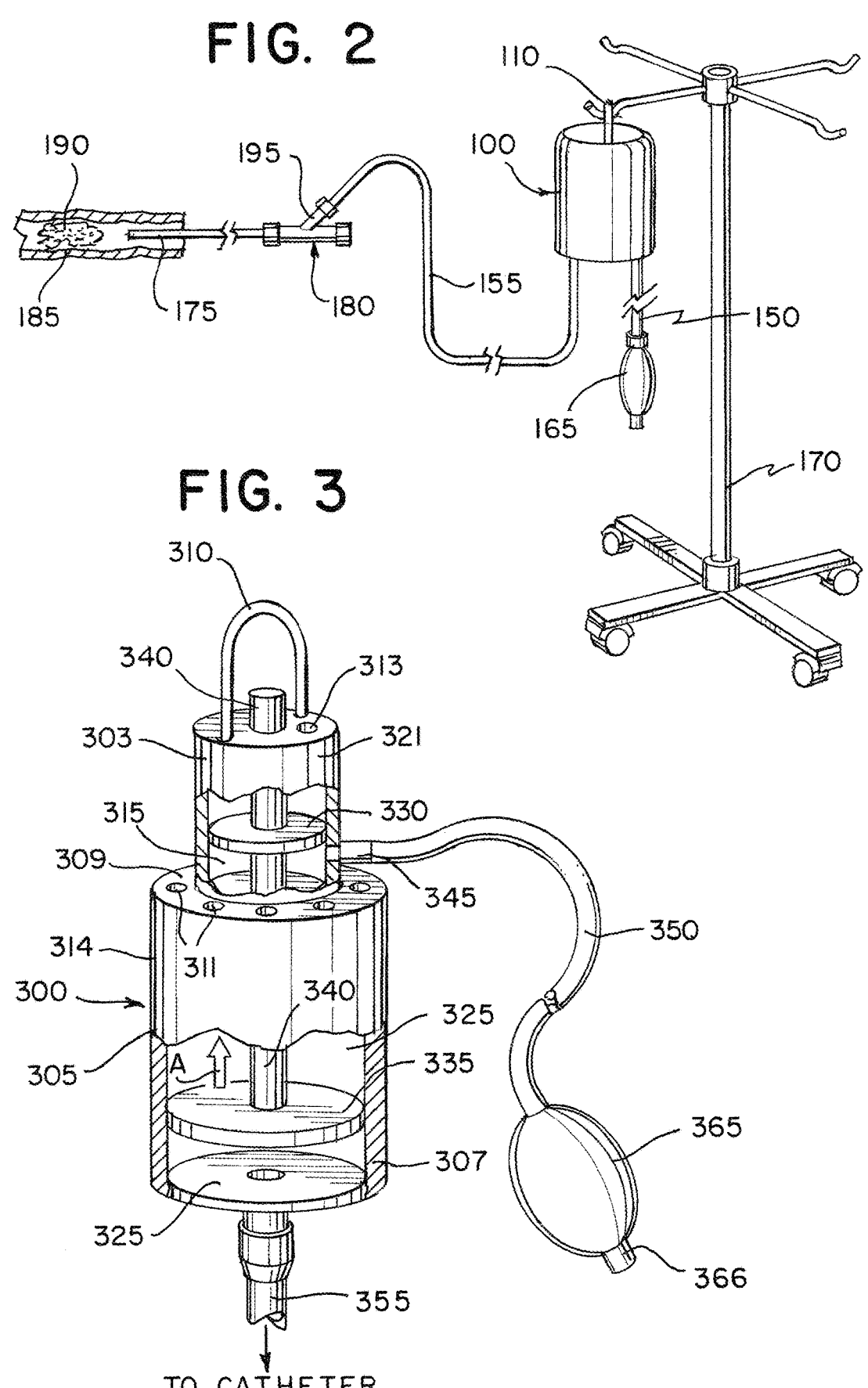
FIG. 2 is a perspective view of the vacuum source hanging from a mobile stand and in fluid connection with an aspiration catheter.
FIG. 3 is a perspective view of another example of a vacuum source hanging from a mobile stand and in fluid connection with an aspiration catheter.

Referring now to FIGS. 1A, 1B and 2, an aspiration vacuum source 100 is illustrated. Vacuum source 100 includes a vessel 105. Vessel 105 has a top end 103 and a bottom end 107 and a partition plate 109 separating the top portion of vessel 105 from the bottom portion of vessel 105. Partition plate 109 separates an internal chamber within vessel 105 into an upper chamber above plate 109 and a lower chamber 125 below plate 109. Lower chamber 125 is also referred to as an aspiration pressure chamber. The top end 103 of vessel 105 has a handle 110 in the form of an elongated opening. Vessel 105 could be, for example, hung from an IV pole in an operating room ("OR") in a manner similar to how an IV bag may hang from an IV pole. Thus, vessel 105 is adapted to be suspendable in air and may be oriented in a vertical direction with the hangable structural feature 110 disposed at the top end. Handle 110 can be, for example, a hook, an open loop, or a closed loop as is illustrated in FIG. 1A. Vessel 105 further includes a fluid storage reservoir 115. Primary tubing 150 is in fluid communication with the fluid storage reservoir 115. A first valve 145 is disposed within vessel 100 and connects fluid reservoir 115 to tubing 150. First valve 145 is a one-way check valve that restricts flow therethrough to only flow downstream from the fluid storage reservoir 115. Secondary tubing 155 is in fluid communication with a lower chamber 125. More specifically, secondary tubing 155 is in fluid communication with the portion of lower chamber 125 that is below piston 135.

A positive pressure fluid chamber 120 is fluidly connected to primary tubing 150 via an auxiliary tubing 160. Auxiliary tubing 160 has a second one-way check valve 145' disposed therein restricting flow therethrough to only flow upstream into the positive pressure fluid chamber 120. Valves 145 and 145' are preferably self-closing non-return (or one-way) valves as shown in FIG. 1B. A fluid piston 130 is slidable within the positive pressure fluid chamber 120. Vessel 105 also included an vacuum chamber 125 in the bottom end 107 of vessel 105. Chamber 125 is not in fluid communication with the positive pressure fluid chamber 120. A vacuum piston 135 is slidably received in chamber 125. As shown in FIG. 1, fluid piston 130 and vacuum piston 135 are fixedly connected to each other by an inverted J-shaped common shaft 140. Alternatively, fluid piston 130 and vacuum piston 125 can be fixedly connected to each other by other mechanisms, such as, for example, a rack and pinion gear assembly or a gear and pulley arrangement (not shown). As shown in FIG. 1, shaft 140 can move up or down within vessel 105. Shaft 140 is in sliding, sealing contact with plate 109. A manual pump 165 is connected in fluid communication with the primary tubing 150. Manual pump 165 can be, for example, a pressure bulb as is known in the art. A user can manipulate bulb 165 by, for example, squeezing bulb manually to create a fluid pressure within tubing 150. Because of check valves 145, 145' fluid within tubing 150 will pass by check valve 145' but is prevented from passing by check valve 145. Thus, upon manipulation of bulb 165, fluid will accumulate in chamber 120 thereby causing piston 130 to move upwards. The fluid within tubing 150 can be, for example, a liquid or a gas. In one example, the fluid is saline. Movement of piston 130 causes movement of piston 135 in the same direction. Thus, squeezing bulb 165 will cause fluid to enter chamber 120 thereby causing piston 130 to move upwards in the direction indicated by arrow A in FIG. 1A. Thus, bulb 165 acts as a manual pump. Upward movement of piston 130 causes upward movement of piston 135, which creates a vacuum in secondary tubing 155. Partition plate 109 has some vent holes 111 therein. Likewise, the walls of vessel 105 also has a vent opening 113 at a location above partition plate 109 so that as piston 135 moves upwards or downwards, piston 135 doesn't meet resistance from air or other fluid trapped within vessel 105 above piston 135.

Primary tubing 150, auxiliary tubing 160, fluid storage reservoir 115, and positive pressure fluid chamber 120 together form a closed system in fluid communication with one another. This closed system contains a constant volume of fluid, when the fluid is a liquid, like, for example, saline. displaceable within the closed system in response to operation of the manual pump (165) that increases pressure imposed on the fluid.

Vessel 105 may have a rigid housing throughout. At a minimum, vessel 105 has rigid housing walls below partition plate 109 so that lower chamber 125 is rigid in order to maintain a vacuum without deforming. The upper portion of vessel 105 could be made from a flexible bag, like a traditional saline bag, which expands as the piston rises unless there are vent openings 113 in the upper portion of vessel 105 as shown in FIG. 1A.

As shown in FIG. 2, aspiration vacuum source 100 can be suspended from a mobile pole or stand 170 via hangable structural feature 110. Vacuum source 100 can be disposable following a single use or multiple repeated uses as vessel 105 may be contaminated with body fluids during use. As shown in FIG. 2, secondary tubing 155 is fluidly connected to an aspiration catheter 175 via an aspiration port 195 of a proximal hub 180. Aspiration catheter can be delivered to a site within a vessel 185 of a patient to remove a clot 190 lodged within vessel 185. Upon placing a distal end of aspiration catheter 175 adjacent to and proximal to clot 190, a user may manipulate bulb 165 by squeezing bulb repeatedly to apply a vacuum pressure within tubing 155 and thus within aspiration catheter 175 to aid in removing clot 190 from vessel 185.

Referring now to FIG. 3, another example of a vacuum source 300 in accordance with the present disclosure is illustrated. Vacuum source 300 includes a vessel 305. Vessel 305 has a top end 303 and a bottom end 307 and a partition plate 309 separating the top portion of vessel 305 from the bottom portion of vessel 305. Partition plate 309 separates an internal chamber within vessel 305 into an upper chamber above plate 309 and a lower chamber 325 below plate 309. Lower chamber 325 is also referred to as an aspiration pressure chamber. The top end 303 of vessel 305 has a handle 310 in the form of an inverted U-shaped handle that can be hung on a stand 170. Vessel 305 could be, for example, hung from an IV pole 170 in an operating room ("OR") in a manner like how an IV bag may hang from an IV pole. Thus, vessel 305 is adapted to be suspendable in air and may be oriented in a vertical direction with the hangable structural feature 310 disposed at the top end. Handle 310 can be, for example, a hook, an open loop, or a closed loop as is illustrated in FIG. 3. Vessel 305 has a cylindrical housing 321 disposed at a top portion of vessel 305 above plate 309 and another cylindrical housing 314 disposed at a bottom portion of vessel 305 below plate 309. A shaft 340 is fixedly connected to piston 330 disposed within housing 321 and to piston 335 disposed within housing 314. A fluid reservoir or chamber 315 has plate 309 as its lower surface, a lower surface of piston 330 as its upper surface and an inner surface of housing 314 as its cylindrical side surface between plate 309 and piston 330. Primary tubing 350 is in fluid communication with the fluid storage reservoir 315. A first valve 345 is disposed within tubing 350 and connects fluid reservoir 315 to tubing 350. First valve 345 is a one-way check valve that restricts flow therethrough to only flow downstream from the fluid storage reservoir 315. A secondary tubing 355 is in fluid communication with a lower chamber 325. More specifically, secondary tubing 355 is in fluid communication with the portion of lower chamber 325 that is below piston 335.

A manual pump 365 is connected in fluid communication with the primary tubing 350. Manual pump 365 can be, for example, a pressure bulb as is known in the art. A user can manipulate bulb 365 by, for example, squeezing bulb manually to create a fluid pressure within tubing 350. Bulb 365 has a one-way valve 366 at its end opposite a connection with tubing 350. Because of check valves 345 and 366 fluid within tubing 350 will pass by check valve 345 but is prevented from passing by check valve 366. Thus, upon manipulation of bulb 365, fluid will accumulate in chamber 315 thereby causing piston 330 to move upwards. The fluid within tubing 350 can be, for example, a liquid or a gas. In one example, the fluid is saline. In another example, the fluid can be air. Movement of piston 330 causes movement of piston 335 in the same direction. Thus, squeezing bulb 365 will cause fluid to enter chamber 320 thereby causing piston 330 to move upwards in the direction indicated by arrow A in FIG. 3. Thus, bulb 365 acts as a manual pump. Upward movement of piston 330 causes upward movement of piston 335, which creates a vacuum in secondary tubing 355. Partition plate 309 has some vent holes 311 therein. Likewise, the walls of vessel 305 also has a vent opening 313 at a location above partition plate 309 so that as piston 335 moves upwards or downwards, piston 335 doesn't meet resistance from air or other fluid trapped within vessel 305 above piston 335.

Referring now to FIGS. 4A and 4B, a method for using an aspiration vacuum source is illustrated. In one aspect of the disclosure, the method comprises step 400, in response to manipulation of the bulb 165, 365 increasing pressures imposed on and displacing the fluid in the closed system to flow into the positive pressure chamber 120, 315. At step 405, in response to the displaced fluid flowing into the positive pressure chamber 120, 315 sliding the fluid piston 130, 330 disposed therein. At step 410, in concert with the sliding of the fluid piston 130 in the positive pressure chamber 120, 315 simultaneously sliding the vacuum piston 135, 335 disposed within the aspiration chamber 125, 325. Finally, at step 420, as the vacuum piston 135, 335 slides within the aspiration chamber 125, 325, producing the aspiration pressure in the aspiration chamber 125, 325 and dispensed therefrom via the secondary tubing 155, 355 in fluid communication therewith.

In accordance with another aspect of the disclosure, at step 430, in response to repeated manipulation of the manual pump 165, 365, producing an aspiration source in the vacuum chamber 125, 325 and dispensed via the secondary tubing 155, 355.

In accordance with another aspect of the disclosure, at step 440, prior to manipulating the manual pump 165,365 advancing a distal end of an aspiration catheter 175 through a vessel 185 to a proximal side of a targeted clot 190 to be captured; wherein the secondary tubing 155, 355 of the aspiration vacuum source 100, 300 is connected to an aspiration port 195 of a proximal hub 180 attached to the aspiration catheter 175.

In accordance with another aspect of the disclosure, at step 450, in response to the aspiration pressure being dispensed via the secondary tubing 155, 355 capturing within a lumen of the aspiration catheter 175 the targeted clot 190.

In accordance with another aspect of the disclosure, at step 460, wherein the volume of the aspiration pressure is continuously producible in the aspiration chamber 125 without requiring detachment or replacement of the aspiration vacuum source 100, 300 from the proximal hub 180.

In accordance with another aspect of the disclosure, at step 470, wherein the aspiration vacuum source is universally usable with the aspiration catheter 175 irrespective of configuration.

Aspects of the invention are also provided by the following numbered clauses:

Clause 1. An aspiration vacuum source (100) comprising:
a vessel (105) having a positive pressure fluid chamber and a vacuum chamber;
a primary tubing (150);
the positive pressure fluid chamber (120) connected in fluid communication with the primary tubing (150) via an auxiliary tubing (160); the auxiliary tubing (160) having a first valve (145') disposed therein restricting flow therethrough to only flow upstream into the positive pressure fluid chamber (120);
a fluid piston (130) slidably received within the positive pressure fluid chamber (120);
the vacuum chamber (125) not in fluid communication with the positive pressure fluid chamber (120);
a vacuum piston (135) slidably received within the vacuum chamber (125) and producing a vacuum within the vacuum chamber (125) upon movement of the vacuum piston (135); the fluid piston (130) and the vacuum piston (135) are each fixedly attached to a common shaft (140) to be movable together within the positive pressure fluid chamber (120) and the vacuum chamber (125), respectively;
a secondary tubing (155) connected in fluid communication to the vacuum chamber (125) through which the produced aspiration is dispensable therefrom; and
a manual pump (165) connected in fluid communication with the primary tubing (150); wherein a vacuum is producible in the vacuum chamber (125) in response to repeated manipulation of the manual pump (165).

Clause 2. The aspiration vacuum source in accordance with clause 1, wherein at least a portion of the vessel (105) is a bag.

Clause 3. The aspiration vacuum source in accordance with clause 1, wherein the shaft member (140) is J-shaped.

Clause 4. The aspiration vacuum source in accordance with any of clauses 1-3, further comprising a hangable structural feature (110) at the top end of the vessel (105) when oriented in the vertical direction includes: a handle, a hook, an open loop, or a closed loop.

Clause 5. The aspiration vacuum source in accordance with clause 4, wherein the aspiration vacuum source (100) is suspendable from a mobile pole (170) via the hangable structural feature (110).

Clause 6. The aspiration vacuum source in accordance with any of clauses 1-5, wherein the first valve (145') is a self-closing non-return valves.

Clause 7. The aspiration vacuum source in accordance with any of clauses 1-6, wherein the vessel (105) is repeatably useable.

Clause 8. The aspiration vacuum source in accordance with any of clauses 1-7, wherein the vessel (105) is disposable following a single use or multiple repeated uses.

Clause 9. The aspiration vacuum source in accordance with any of clauses 1-8, further comprising a fluid storage reservoir (115); the primary tubing (150) connected in fluid communication with the fluid storage reservoir (115); the primary tubing (150) having a first valve (145) disposed therein restricting flow therethrough to only flow downstream from the fluid storage reservoir (115).

Clause 10. The aspiration vacuum source in accordance with any of clauses 1-9, wherein the vessel having a top end with a hangable structural feature (110) from which the vessel (105) is adapted to be suspendable in air therefrom; the vessel (105) when hung is oriented in a vertical direction with the hangable structural feature (110) disposed at the top end.

Clause 11. The aspiration vacuum source in accordance with any of clauses 1-10, wherein the primary tubing (150), the auxiliary tubing (155) and the positive pressure fluid chamber (120) together form a closed system in fluid communication with one another; and the closed system contains a constant volume of fluid displaceable within the closed system in response to operation of the manual pump (165) that increases pressure imposed on the fluid.

Clause 12. A method for using an aspiration vacuum source including:

a vessel (105) comprising:

a primary tubing (150);

a positive pressure fluid chamber (120) connected in fluid communication with the primary tubing (150) via an auxiliary tubing (160); the auxiliary tubing (160) having a first valve (145') disposed therein restricting flow therethrough to only flow upstream into the positive pressure fluid chamber (120);

a fluid piston (130) slidably received within the positive pressure fluid chamber (120);

an vacuum chamber (125) not in fluid communication with the positive pressure fluid chamber (120);

a vacuum piston (135) slidably received within and producing an aspiration pressure within the vacuum chamber (125); the fluid piston (130) and the vacuum piston (135) are each fixedly attached to a common shaft (140) to be slidable in concert together within the positive pressure fluid chamber (120) and the vacuum chamber (125), respectively;

a secondary tubing (155) connected in fluid communication to the vacuum chamber (125) through which the produced aspiration is dispensable therefrom; and a manual pump (165) connected in fluid communication with the primary tubing (150); wherein a vacuum is producible in the vacuum chamber (125) in response to repeated manipulation of the manual pump (165);

the method comprising the steps of:

in response to manipulation of the manual pump (165), increasing pressure imposed on and displacing the fluid in the closed system to flow into the positive pressure chamber (120);

in response to the displaced fluid flowing into the positive pressure chamber (120), sliding the fluid piston (130) disposed therein;

simultaneously sliding the vacuum piston (135) disposed within the aspiration chamber (125) in response to the sliding of the fluid piston (130) in the positive pressure chamber (120); and as the vacuum piston (135) slides within the aspiration chamber (125), producing a vacuum in the aspiration chamber (125); wherein the vacuum produced in the aspiration chamber (125) is in fluid communication with the secondary tubing (155).

Clause 13. The method in accordance with clause 12, further comprising, in response to repeated manipulation of the manual pump (165), producing an aspiration source in the vacuum chamber (125) and dispensed via the secondary tubing (155).

Clause 14. The method in accordance with any of clauses 11-13, wherein prior to manipulating the manual pump (165), further comprising the steps of:

advancing a distal end of an aspiration catheter (175) through a vessel (185) to a proximal side of a targeted clot (190) to be captured; wherein the secondary tubing (155) is connected to an aspiration port (195) of a proximal hub (180) attached to the aspiration catheter (175).

Clause 15. The method in accordance any of clauses 11-14, further comprising, in response to the aspiration pressure being dispensed via the secondary tubing (155), capturing within a lumen of the aspiration catheter (175) the targeted clot (190).

Clause 16. The method in accordance any of clauses 11-15, wherein the aspiration is producible in the aspiration chamber (125) without requiring detachment or replacement of the aspiration vacuum source (100) from the proximal hub (180).

Clause 17. The method in accordance with any of clauses 11-16, wherein the vessel (105) is repeatably useable.

Clause 18. The method in accordance with any of clauses 11-16, wherein the vessel (105) is disposable following a single use or multiple repeated uses.

The descriptions contained herein are examples of embodiments of the disclosure and are not intended in any way to limit the scope of the disclosure. As described herein, the disclosure contemplates many variations and modifications of the vacuum source. Modifications and variations apparent to those having skilled in the pertinent art according to the teachings of this disclosure are intended to be within the scope of the claims which follow.

What is claimed is:

1. An aspiration vacuum source comprising:

a vessel having a positive pressure fluid chamber and a vacuum chamber;

a primary tubing;

the positive pressure fluid chamber connected in fluid communication with the primary tubing via an auxiliary tubing; the auxiliary tubing having a first valve disposed therein restricting flow therethrough to only flow upstream into the positive pressure fluid chamber;

a fluid piston slidably received within the positive pressure fluid chamber;

the vacuum chamber not in fluid communication with the positive pressure fluid chamber;

a vacuum piston slidably received within the vacuum chamber and producing a vacuum within the vacuum chamber upon movement of the vacuum piston; the fluid piston and the vacuum piston are each fixedly attached to a common shaft to be movable together within the positive pressure fluid chamber and the vacuum chamber, respectively;

a secondary tubing connected in fluid communication to the vacuum chamber through which the produced aspiration is dispensable therefrom; and a manual pump connected in fluid communication with the primary tubing; wherein a vacuum is producible in the vacuum chamber in response to repeated manipulation of the manual pump.

2. The aspiration vacuum source in accordance with claim 1, wherein at least a portion of the vessel is a bag.

3. The aspiration vacuum source in accordance with claim 1, wherein a shaft member is J-shaped.

4. The aspiration vacuum source in accordance with claim 1, further comprising a hangable structural feature at the top end of the vessel when oriented in the vertical direction includes: a handle, a hook, an open loop, or a closed loop.

5. The aspiration vacuum source in accordance with claim 4, wherein the aspiration vacuum source is suspendable from a mobile pole via the hangable structural feature.

6. The aspiration vacuum source in accordance with claim 1, wherein the first valve is a self-closing non-return valve.

7. The aspiration vacuum source in accordance with claim 1, wherein the vessel is repeatably useable.

8. The aspiration vacuum source in accordance with claim 1, wherein the vessel is disposable following a single use or multiple repeated uses.

9. The aspiration vacuum source in accordance with claim 1, further comprising a fluid storage reservoir; the primary tubing connected in fluid communication with the fluid storage reservoir; the primary tubing having a second valve disposed therein restricting flow therethrough to only flow downstream from the fluid storage reservoir.

10. The aspiration vacuum source in accordance with claim 1, wherein the vessel having a top end with a handle from which the vessel is adapted to be suspendable in air therefrom; the vessel when hung is oriented in a vertical direction with the hangable structural feature disposed at the top end.

11. The aspiration vacuum source in accordance with claim 1, wherein the primary tubing, the auxiliary tubing and the positive pressure fluid chamber together form a closed system in fluid communication with one another; and the closed system contains a constant volume of fluid displaceable within the closed system in response to operation of the manual pump that increases pressure imposed on the fluid.

12. A method for using an aspiration vacuum source including:

a vessel comprising:

a primary tubing;

a positive pressure fluid chamber connected in fluid communication with the primary tubing via an auxiliary tubing; the auxiliary tubing having a valve disposed therein restricting flow therethrough to only flow upstream into the positive pressure fluid chamber;

a fluid piston slidably received within the positive pressure fluid chamber;

a vacuum chamber not in fluid communication with the positive pressure fluid chamber;

a vacuum piston slidably received within and producing an aspiration pressure within the vacuum chamber; the fluid piston and the vacuum piston are each fixedly attached to a common shaft to be slidable in concert together within the positive pressure fluid chamber and the vacuum chamber, respectively;

a secondary tubing connected in fluid communication to the vacuum chamber through which the produced aspiration is dispensable therefrom; and a manual pump connected in fluid communication with the primary tubing; wherein a vacuum is producible in the vacuum chamber in response to repeated manipulation of the manual pump;

the method comprising the steps of:

in response to manipulation of the manual pump, increasing pressure imposed on and displacing a fluid in a closed system to flow into the positive pressure chamber;

in response to the displaced fluid flowing into the positive pressure chamber, sliding the fluid piston disposed therein;

simultaneously sliding the vacuum piston disposed within the aspiration chamber in response to the sliding of the fluid piston in the positive pressure chamber; and as the vacuum piston slides within the aspiration chamber, producing a vacuum in the aspiration chamber; wherein the vacuum produced in the aspiration chamber is in fluid communication with the secondary tubing.

13. The method in accordance with claim 12, further comprising, in response to repeated manipulation of the manual pump, producing an aspiration source in the vacuum chamber and dispensed via the secondary tubing.

14. The method in accordance with claim 13, wherein prior to manipulating the manual pump further comprising the steps of:

advancing a distal end of an aspiration catheter through a vessel to a proximal side of a targeted clot to be captured; wherein the secondary tubing is connected to an aspiration port of a proximal hub attached to the aspiration catheter.

15. The method in accordance with claim 14, further comprising, in response to the aspiration pressure being dispensed via the secondary tubing, capturing within a lumen of the aspiration catheter the targeted clot.

16. The method in accordance with claim 15, wherein the aspiration is producible in the aspiration chamber without requiring detachment or replacement of the aspiration vacuum source from the proximal hub.

17. The method in accordance with claim 13, wherein the vessel is repeatably useable.

18. The method in accordance with claim 13, wherein the vessel is disposable following a single use or multiple repeated uses.

* * * * *